US009275471B2

(12) United States Patent
Hamilton (10) Patent No.: US 9,275,471 B2
(45) Date of Patent: Mar. 1, 2016

(54) METHOD FOR ULTRASOUND MOTION TRACKING VIA SYNTHETIC SPECKLE PATTERNS (75) Inventor: James Hamilton, Brighton, MI (US)

(73) Assignee: Ultrasound Medical Devices, Inc., Ann Arbor, MI (US)

(*) Notice: Subject to any disclaimer, the term of this patent is extended or adjusted under 35 U.S.C. 154(b) by 225 days.

(21) Appl. No.: 12/859,096

(22) Filed: Aug. 18, 2010

(65) Prior Publication Data
US 2011/0263981 A1 Oct. 27, 2011

Related U.S. Application Data (60) Provisional application No. 61/327,505, filed on Apr. 23, 2010.

(51) Int. Cl.
G06T 7/20 (2006.01)
A61B 8/08 (2006.01)

(52) U.S. Cl.
CPC .............. *G06T 7/2033* (2013.01); *A61B 8/08* (2013.01); *G06T 2207/10132* (2013.01); *G06T 2207/30004* (2013.01)

(58) Field of Classification Search
CPC ........................................... G06T 2207/10132
USPC ..................... 600/437, 443; 73/606
See application file for complete search history.

(56) References Cited

U.S. PATENT DOCUMENTS

| 4,265,126 A | 5/1981 | Papadofrangakis et al. |
| 5,503,153 A | 4/1996 | Liu et al. |
| 5,582,173 A | 12/1996 | Li |
| 5,675,554 A | 10/1997 | Cole et al. |
| 5,701,897 A * | 12/1997 | Sano .............................. 600/453 |
| 5,749,367 A | 5/1998 | Gamlyn et al. |
| 5,800,356 A | 9/1998 | Criton et al. |
| 5,873,830 A | 2/1999 | Hossack et al. |
| 5,876,342 A | 3/1999 | Chen et al. |
| 5,934,288 A | 8/1999 | Avila et al. |
| 5,976,088 A | 11/1999 | Urbano et al. |

(Continued)

FOREIGN PATENT DOCUMENTS

| EP | 1249208 A | 10/2002 |
| EP | 1005834 B1 | 4/2007 |

(Continued)

OTHER PUBLICATIONS

Bons et al., "Speckle tracking for multi-dimensional flow estimation," Elsevier Science B.V., Ultrasonics vol. 38 p. 369-375, Mar. 1, 2000.

(Continued)

*Primary Examiner* — Amanda Lauritzen Moher
*Assistant Examiner* — Serkan Akar
(74) *Attorney, Agent, or Firm* — Christopher L. E. Hines; Polsinelli PC (57) ABSTRACT A method for measuring motion from biological imaging data including collecting non-carrier data images; patterning the non-carrier data images with synthetic carrier properties; and processing the patterned non-carrier data images with a carrier based motion tracking technique to generate images representing motion measurements. The method preferably converts images lacking a carrier signal to ones with a synthetic carrier signal such that highly accurate and robust speckle tracking can be achieved.

8 Claims, 14 Drawing Sheets

(56) References Cited

U.S. PATENT DOCUMENTS

| | | | |
|---|---|---|---|
| 6,014,473 A | 1/2000 | Hossack et al. | |
| 6,015,385 A | 1/2000 | Finger et al. | |
| 6,042,547 A | 3/2000 | Wright et al. | |
| 6,050,946 A | 4/2000 | Teo | |
| 6,056,691 A | 5/2000 | Urbano et al. | |
| 6,066,095 A | 5/2000 | Morsy et al. | |
| 6,083,168 A | 7/2000 | Hossack et al. | |
| 6,099,471 A | 8/2000 | Torp et al. | |
| 6,142,946 A | 11/2000 | Hwang et al. | |
| 6,162,174 A | 12/2000 | Friemel | |
| 6,166,853 A | 12/2000 | Sapia et al. | |
| 6,201,900 B1 | 3/2001 | Hossack et al. | |
| 6,210,333 B1 | 4/2001 | Gardner et al. | |
| 6,213,947 B1 | 4/2001 | Phillips | |
| 6,228,028 B1 | 5/2001 | Klein et al. | |
| 6,254,541 B1 | 7/2001 | Teo | |
| 6,270,459 B1 | 8/2001 | Konofagu et al. | |
| 6,277,075 B1 | 8/2001 | Torp et al. | |
| 6,282,963 B1 | 9/2001 | Haider | |
| 6,312,381 B1 | 11/2001 | Knell et al. | |
| 6,318,179 B1* | 11/2001 | Hamilton et al. | 73/606 |
| 6,346,079 B1 | 2/2002 | Haider et al. | |
| 6,350,238 B1 | 2/2002 | Olstad et al. | |
| 6,352,507 B1 | 3/2002 | Torp et al. | |
| 6,360,027 B1 | 3/2002 | Hossack et al. | |
| 6,364,835 B1* | 4/2002 | Hossack et al. | 600/443 |
| 6,406,430 B1 | 6/2002 | Ishrak et al. | |
| 6,443,894 B1 | 9/2002 | Sumanaweera et al. | |
| 6,447,450 B1 | 9/2002 | Olstad | |
| 6,447,453 B1 | 9/2002 | Roundhill et al. | |
| 6,447,454 B1 | 9/2002 | Chenal et al. | |
| 6,464,643 B1 | 10/2002 | Brock-Fisher | |
| 6,520,913 B1 | 2/2003 | Pesavento et al. | |
| 6,527,717 B1 | 3/2003 | Jackson et al. | |
| 6,537,217 B1 | 3/2003 | Bjærum et al. | |
| 6,537,221 B2 | 3/2003 | Criton et al. | |
| 6,638,221 B2 | 10/2003 | Abe et al. | |
| 6,666,823 B2 | 12/2003 | Yao | |
| 6,676,599 B2 | 1/2004 | Torp et al. | |
| 6,676,603 B2 | 1/2004 | Aichhorn et al. | |
| 6,773,403 B2 | 8/2004 | Kim et al. | |
| 6,776,759 B2 | 8/2004 | Heimdal et al. | |
| 6,976,961 B2 | 12/2005 | Jackson et al. | |
| 6,994,673 B2 | 2/2006 | Lysyansky et al. | |
| 7,033,320 B2 | 4/2006 | Von Behren et al. | |
| 7,077,807 B2 | 7/2006 | Torp et al. | |
| 7,088,850 B2 | 8/2006 | Wei et al. | |
| 7,131,947 B2 | 11/2006 | Demers | |
| 7,448,998 B2 | 11/2008 | Robinson | |
| 7,536,043 B2 | 5/2009 | Fan et al. | |
| 7,894,874 B2 | 2/2011 | Lynch et al. | |
| 7,983,456 B2 | 7/2011 | Rao et al. | |
| 7,998,074 B2 | 8/2011 | Chomas et al. | |
| 2003/0021945 A1 | 1/2003 | Kelch | |
| 2003/0036701 A1 | 2/2003 | Dong et al. | |
| 2003/0063775 A1 | 4/2003 | Rafii et al. | |
| 2003/0158483 A1 | 8/2003 | Jackson et al. | |
| 2004/0006273 A1 | 1/2004 | Kim et al. | |
| 2004/0208341 A1 | 10/2004 | Zhoe et al. | |
| 2004/0267117 A1 | 12/2004 | Wright et al. | |
| 2005/0049496 A1* | 3/2005 | Guracar | 600/437 |
| 2005/0080336 A1 | 4/2005 | Byrd et al. | |
| 2005/0096538 A1 | 5/2005 | Chomas et al. | |
| 2005/0096543 A1 | 5/2005 | Jackson et al. | |
| 2005/0288589 A1 | 12/2005 | Houle et al. | |
| 2006/0002601 A1 | 1/2006 | Fu et al. | |
| 2006/0293598 A1 | 12/2006 | Fraser | |
| 2007/0016031 A1 | 1/2007 | Mourad et al. | |
| 2007/0253599 A1 | 11/2007 | White et al. | |
| 2007/0255137 A1* | 11/2007 | Sui et al. | 600/443 |
| 2007/0276236 A1 | 11/2007 | Jong | |
| 2008/0009722 A1* | 1/2008 | Simopoulos et al. | 600/437 |
| 2008/0019609 A1 | 1/2008 | Hamilton et al. | |
| 2008/0021319 A1 | 1/2008 | Hamilton | |
| 2008/0021945 A1 | 1/2008 | Hamilton et al. | |
| 2008/0077013 A1 | 3/2008 | Kawagishi et al. | |
| 2008/0114250 A1 | 5/2008 | Urbano et al. | |
| 2008/0125657 A1 | 5/2008 | Chomas et al. | |
| 2008/0214934 A1 | 9/2008 | Lee et al. | |
| 2009/0156934 A1 | 6/2009 | Lee et al. | |
| 2010/0081937 A1 | 4/2010 | Hamilton | |
| 2010/0086187 A1 | 4/2010 | Hamilton | |
| 2010/0138191 A1 | 6/2010 | Hamilton | |
| 2010/0185085 A1 | 7/2010 | Hamilton | |
| 2010/0185093 A1* | 7/2010 | Hamilton | 600/443 |
| 2010/0246911 A1* | 9/2010 | Rabben et al. | 382/131 |
| 2011/0263981 A1 | 10/2011 | Hamilton | |

FOREIGN PATENT DOCUMENTS

| | | |
|---|---|---|
| EP | 1489972 B1 | 11/2009 |
| WO | 2010039555 A | 4/2010 |
| WO | 2010039556 A | 4/2010 |
| WO | 2010083468 A | 7/2010 |
| WO | 2010083469 A | 7/2010 |
| WO | 2011133171 A | 10/2011 |

OTHER PUBLICATIONS

Chen et. al. "Lateral Speckle Tracking Using Synthetic Lateral Phase," IEEE transactions on ultrasonics, ferroelectrics, and frequency control, vol. 51, No. 5, May 2004.

D'Hodge et al., "Regional Strain and Strain Rate Measurements by Cardiac Ultrasound: Principles, Implementation and Limitations," The European Society of Cardiology p. 145-170 Jun. 23, 2009.

Kaluzynski et al., "Strain Rate Imaging Using Two-dimensional Speckle Tracking," IEEE Transactions on Ultrasonics, Ferroelectrics, and Frequency Control p. 1111-1123, Jul. 1, 2001.

Li et al., "High resolution 2-D quantification of myocardial motion abnormalities in mice using high resolution ultrasound with MRI validation," Biomedical Imaging: Nano to Macro, 3rd EIII International Symposium on Apr. 6-9, 2006.

D'Hodge, J., et al."Regional Strain and Strain Rate Measurments by Cardiac Ultrasound: Principles, Implementation and Limitations" The European Society of Cardiology p. 145-170 Jun. 23, 2009.

U.S. Appl. No. 12/565,662, filed Sep. 2009, Hamilton.
U.S. Appl. No. 12/565,666, filed Sep. 2009, Hamilton.
U.S. Appl. No. 12/625,875, filed Nov. 2009, Hamilton.
U.S. Appl. No. 12/688,787, filed Jan. 2010, Hamilton.
U.S. Appl. No. 12/625,885, filed Nov. 2009, Hamilton.

Kaluzynski, K., et al. "Strain Rate Imaging Using Two-dimensional Speckle Tracking" IEEE Transactions on Ultrasonics, Ferroelectrics, and Frequency Control p. 1111-1123 Jul. 1, 2001.

L.N. Bohs et al., "Speckle tracking for multi-dimensional flow estimation" Elsevier Science B.V., Ultrasonics vol. 38 p. 369-375 Mar. 1, 2000.

Chen et. al. Lateral Speckle Tracking Using Synthetic Lateral Phase IEEE transactions on ultrasonics, ferroelectrics, and frequency control, vol. 51, No. 5, May 2004.

* cited by examiner

METHOD FOR ULTRASOUND MOTION TRACKING VIA SYNTHETIC SPECKLE PATTERNS

CROSS-REFERENCE TO RELATED APPLICATIONS

This application claims the benefit of U.S. Provisional Application No. 61/327,505, filed 23 Apr. 2010, titled "METHOD FOR MEASURING ULTRASOUND IMAGE MOTION WITH SYNTHETIC SPECKLE PATTERNS", which is incorporated in its entirety by this reference.

This application is related to U.S. patent Ser. No. 11/781,212 filed on Jul. 20, 2007 and entitled "Method of Tracking Speckle Displacement Between Two Images", (2) U.S. patent Ser. No. 11/781,217 filed on Jul. 20, 2007 and entitled "Method of Modifying Data Acquisition Parameters of an Ultrasound Device", (3) U.S. patent Ser. No. 11/781,223 filed on Jul. 20, 2007 and entitled "Method of Processing Spatial-Temporal Data Processing", (4) U.S. patent Ser. No. 12/565,662 filed on Sep. 23, 2009 and entitled "System and Method for Flexible Rate Processing of Ultrasound Data", (5) U.S. patent Ser. No. 12/625,875 filed on Nov. 25, 2009 and entitled "Dynamic Ultrasound Acquisition and Processing Using Object Motion Calculation", (6) U.S. patent Ser. No. 12/688,787 filed on Jan. 15, 2010 and entitled "System and Method for Tissue Motion Measurement Using 3D Ultrasound", and (7) U.S. patent Ser. No. 12/625,885 filed on Nov. 25, 2009 and entitled "Dynamic Ultrasound Acquisition and Processing Using Object Motion Calculation", which are all incorporated in their entirety by this reference.

TECHNICAL FIELD

This invention relates generally to the physiological motion processing field, and more specifically to a new and useful method for measuring image motion with synthetic speckle patterns in the physiological motion processing field.

BACKGROUND

Traditional ultrasound speckle tracking relies on pattern matching algorithms to follow speckles. The speckles are produced from the interaction of the ultrasound signal with tissue micro-structure. Local tissue displacement is calculated through a series of image frames. If raw, radio-frequency (RF) data is used, the ultrasound carrier signal can be used to provide highly accurate (sub-acoustic wavelength) and robust displacement measurements due to the carrier frequency property of RF data. However, there are many forms of ultrasound images and other physiological imaging data that have no carrier information, like B-mode and magnitude images. Tracking using non-carrier ultrasound data requires different methods than established RF based tracking algorithms. Current algorithms for processing non-carrier imaging data have poor performance and high computational demand. Thus, there is a need in the physiological motion processing field to create a new and useful method for measuring image motion with synthetic speckle patterns in the physiological motion processing field. This invention provides such a new and useful method.

DESCRIPTION OF THE PREFERRED EMBODIMENTS

The following description of the preferred embodiments of the invention is not intended to limit the invention to these preferred embodiments, but rather to enable any person skilled in the art to make and use this invention.

Figure 1:
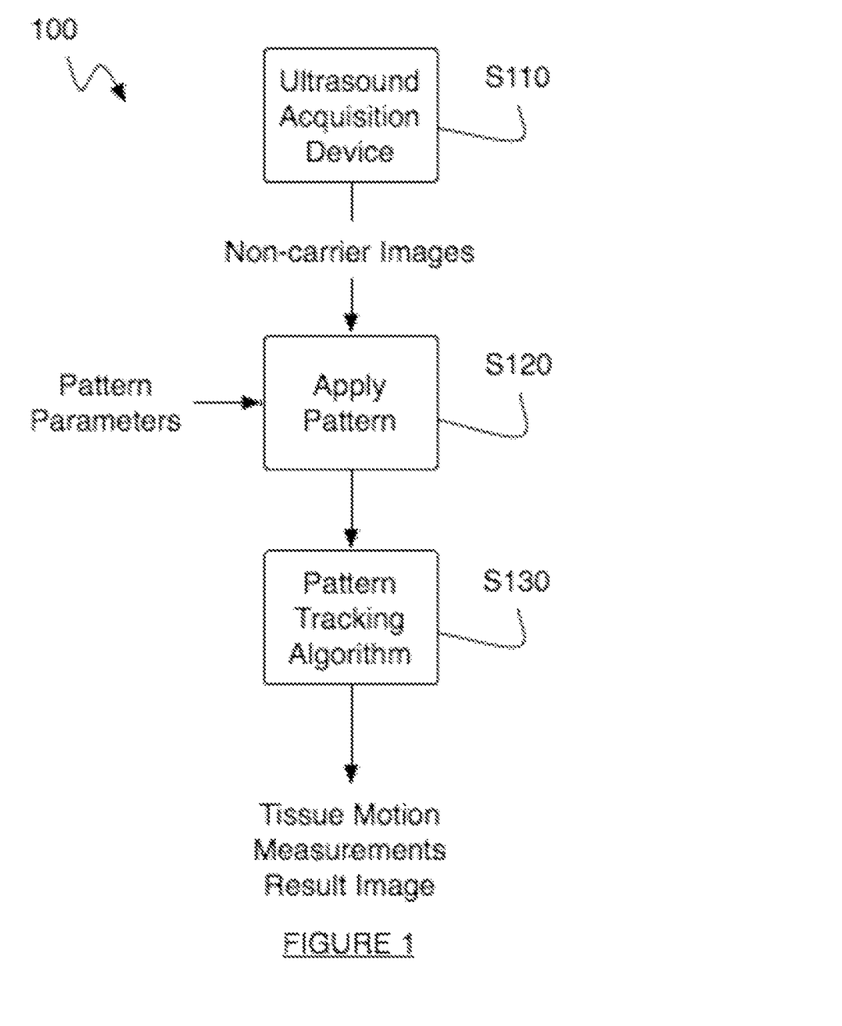
FIG. 1 is a schematic representation of a first preferred embodiment of the invention.

As shown in FIG. 1, a method 100 of the preferred embodiment includes collecting non-carrier data images S110, patterning the non-carrier data images with an applied pattern S120, and processing the patterned non-carrier data images to generate motion measurements (e.g., motion data images) S130. The method 100 functions to calculate tissue motion by inducing a synthetic (artificial) pattern on images that lack such patterning. The method 100 is preferably defined by a transformation of a plurality of non-carrier data images, representing position and structure of a biological object(s), to motion images (i.e. a data image representing a motion measurement of the tissue) generated from a carrier based technique. Tracking techniques of carrier based data images care preferably used for motion tracking of patterned non-carrier data images. RF motion tracking algorithms, such as speckle tracking, preferably rely on an ultrasound carrier signal that can preferably be used to provide highly accurate (e.g., sub-acoustic wavelength) and robust measurements. The method preferably converts images lacking a carrier signal to ones with a synthetic carrier (i.e., the pattern) such that highly accurate and robust speckle tracking can be achieved. For example, non-carrier ultrasound images such as B-mode and magnitude images can preferably be patterned so that tracking algorithms for radio-frequency (RF) data can be used to calculated tissue motion. The method can preferably be used on any suitable data such as Magnetic Resonance Imaging (MRI) data, cardiac computed tomography (CT) scans or any suitable physiological data images (medical images) that could benefit from motion tracking. The method 100 is preferably used on ultrasound data captured to track the motion of tissue. The method 100 preferably enables 2D (two dimensional) motion tracking but may alternatively be applied to any suitable application such as partial 3D ultrasound data.

Step S110, collecting non-carrier data images, functions to collect data that lacks carrier information commonly found in RF data. The non-carrier data images are preferably B-mode ultrasound images (shown in FIG. 2), but may alternatively be pulse magnitude images, RF magnitude images, MRI images, cardiac CT scans, and/or any suitable format that lacks a carrier frequency. Non-carrier data images can additionally be described as amplitude or intensity images. In the case of ultrasound, the non-carrier images re preferably obtained by measuring a pulse envelope of a signal. The data images may additionally be in a variety of formats. In one variation, the images are scan converted wherein the pixels of the image correspond to object space. In another variation, the images are acoustic beam formatted wherein the pixels of the image correspond to imaging space such as angle, range, and/or location. The data images preferably represent biological object or tissue motion such as data related to heart tissue motion. The data images are preferably acquired with any suitable device such as an ultrasound device, a CT scanner, and MRI machine. The device preferably captures 2D images but may alternatively capture 3D images, partial volume 3D images (i.e., 2.5 dimensional images), and/or any suitable type of data images.

Figure 7:
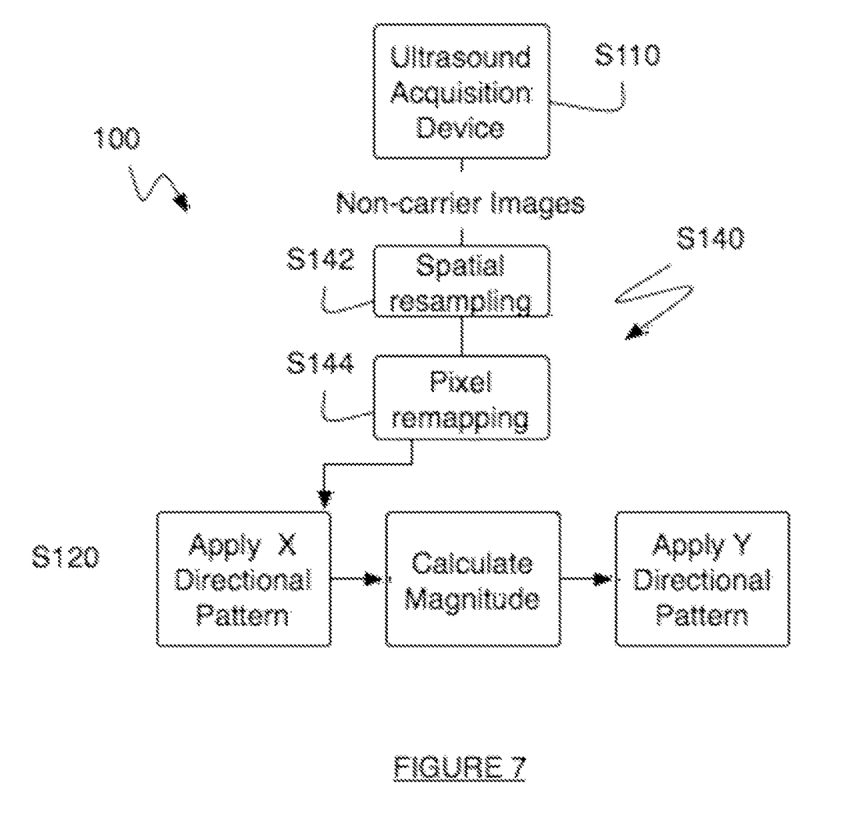
FIG. 7 is a detailed schematic representation of a variation with a patterned image of first coordinate used to pattern an image of a second coordinate.

Step S120, patterning the non-carrier data images with an applied pattern, functions to synthetically tag the non-carrier images with carrier properties. Step S120 preferably converts the non-carrier images to an image with a synthetic carrier frequency such that RF-based tracking algorithms can be used. The pattern applied to the images is preferably generated by applying a complex, finite impulse response (FIR) filter or infinite impulse response (IIR) filter to the images, but may alternatively be any suitable filter. In one example, the filter preferably patterns the data image according to amplitude changes (e.g., edges) of the non-carrier data image. The FIR filter preferably creates real and imaginary components of the pattern signal. The FIR filter preferably is defined by center frequency and bandwidth parameters, but may alternatively be defined by any suitable pattern parameters. The filter preferably determines the pattern carrier frequency and the pulse width (i.e., resolution). Alternatively, an infinite impulse response (IIR) filter may be used and/or any suitable filter or pattern that creates a carrier signal suitable for RF-based tracking algorithms. The pattern can preferably be applied to different directional coordinates/components (e.g., x, y, and/or z direction) of the ultrasound image. The directional components of an image can be patterned and/or processed independently (i.e., separately, in parallel, in series, etc.) and/or jointly (i.e., at the same time), as discussed below. As an additional alternative the patterned data image of a first coordinate is preferably magnitude detected and used as the input data image of a second coordinate as shown in FIG. 7.

Figure 8A:
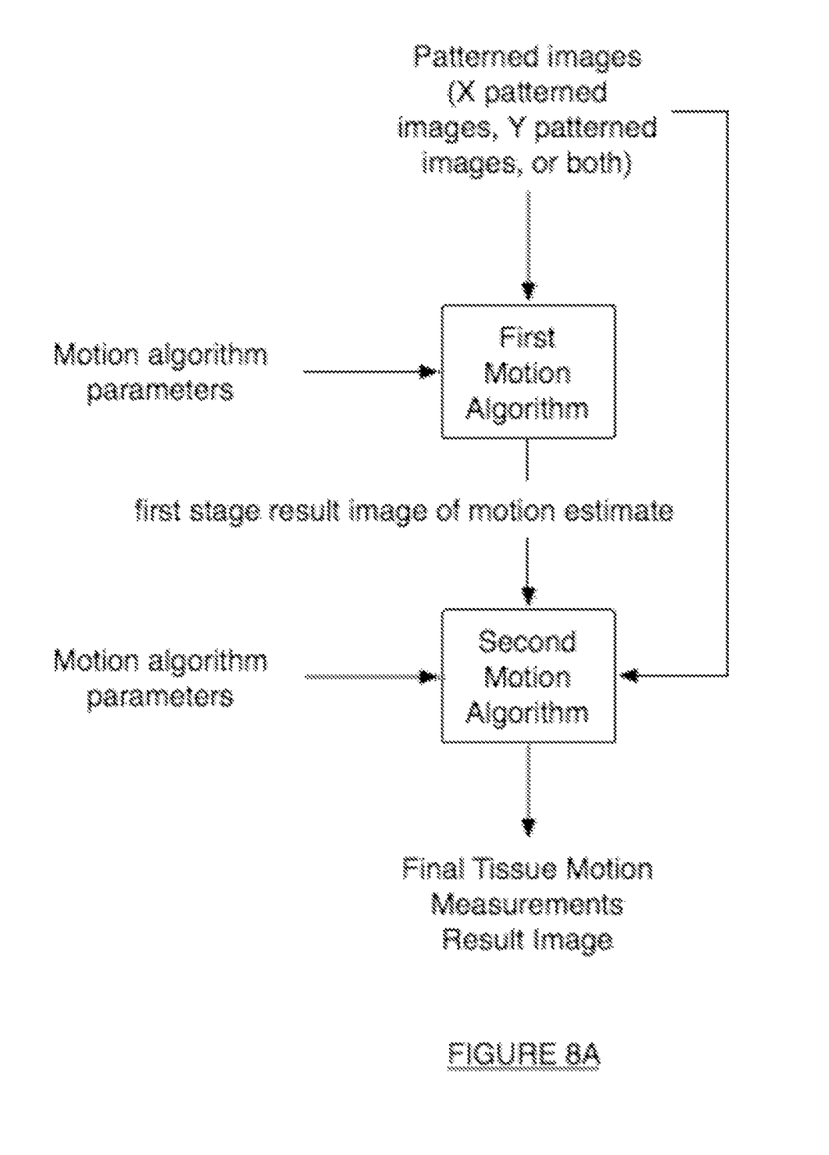
FIGS. 8A-8C is a schematic representation of multi-stage motion tracking.
Figure 8B:
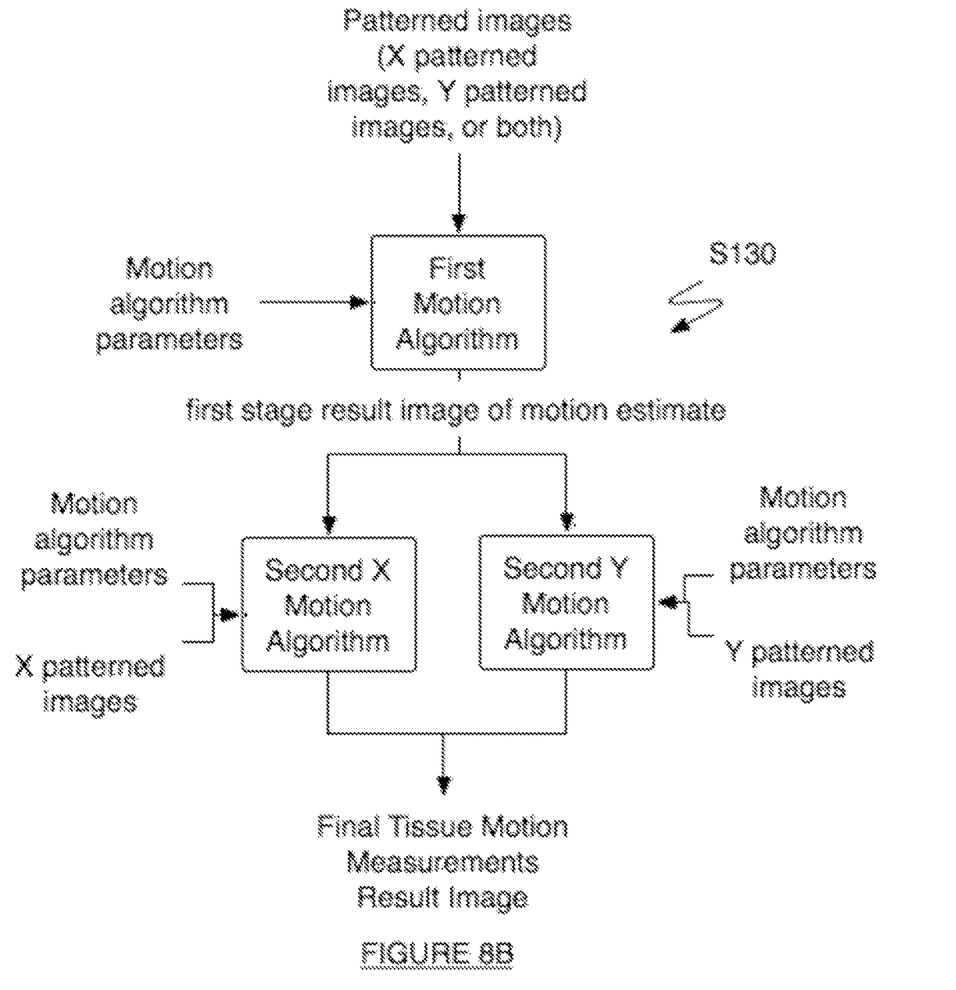
Figure 8C:
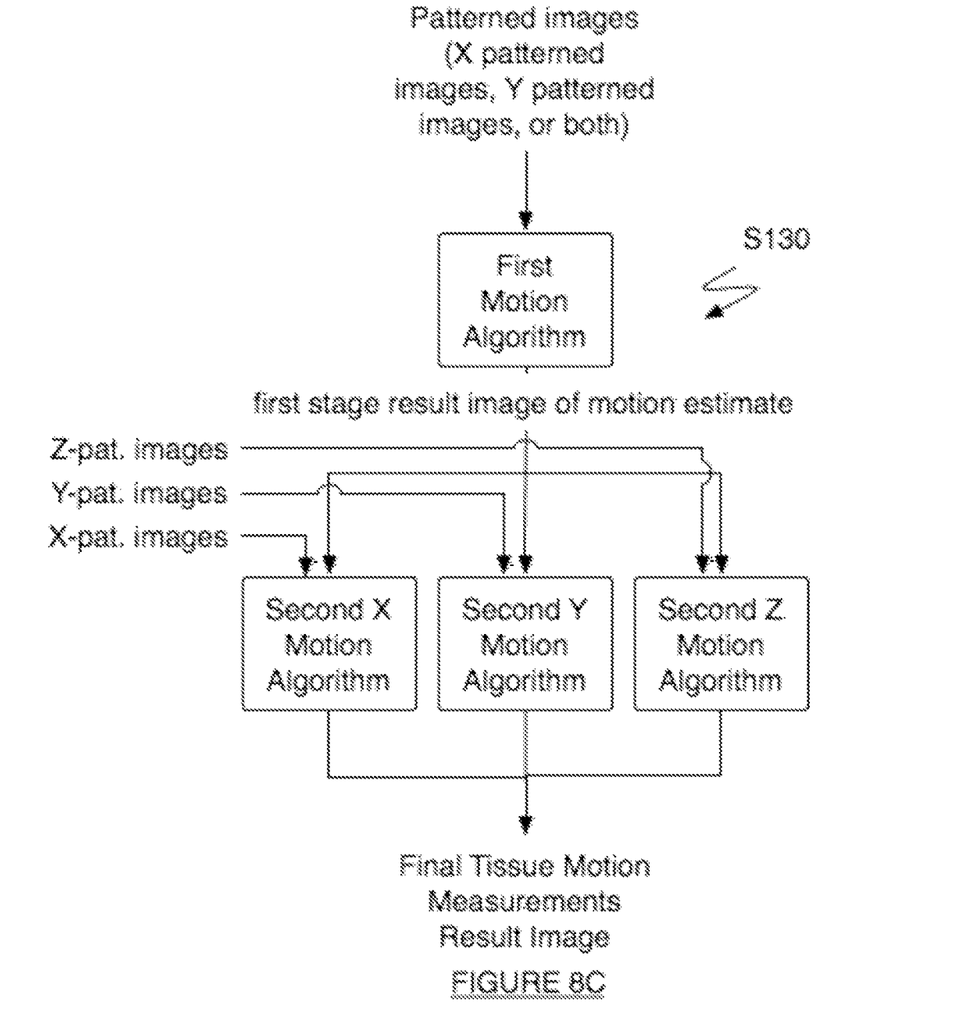

Step S130, processing the patterned non-carrier data images to generate motion images, functions to use the patterned non-carrier images to output tissue motion measurements in the form of a result image. The motion images are preferably multi-dimensional data images of motion estimates (i.e., motion images), though the motion images may alternatively be any suitable data format representing motion estimates of the tissue or object of interest. The motion images preferably represent the motion data but may alternatively be further converted into visual representations of motion. The algorithms used in the calculation are preferably those generally used for carrier encoded ultrasound images. An algorithm for RF speckle tracking is preferably used, though any suitable algorithm may alternatively be used. The measured motion may relate to a measurement of tissue velocity, displacement, acceleration, strain, strain rate, or any suitable characteristic of probe, tissue motion, or tissue deformation. The calculation of pattern motion is preferably a carrier data based motion tracking technique, and more preferably is an RF motion tracking technique. At least two data sets (e.g., data images) acquired at different times are preferably used to calculate 1D, 2D or 3D motion. Speckle tracking is preferably used, but any suitable carrier based tracking method may be used. The motion measurements may additionally be improved and refined using models of tissue motion. As will be described below, some variations will include separately calculating motion for a particular coordinate such as the x-coordinate and y-coordinate. Another variation, as shown in FIGS. 8A-8C, preferably includes processing the patterned non-carrier data images in a plurality of stages by calculating a motion image (i.e., processing the patterned data images) with a first set of tracking parameters and calculating a motion image with a second set of tracking parameters. This variation of multi-stage motion tracking preferably functions to enable refinement of motion images. The at least two stages of processing preferably use differing sets of motion tracking parameters (e.g., speckle tracking parameters). Tracking parameters preferably includes properties such as kernel size, search range (i.e., distance), correlation filter, displacement filter, or any suitable tracking parameter. Each stage is preferably tuned for desired performance. Additionally, a second stage may utilize the motion calculated in the first stage of processing to further refine the processing. In one example, the first stage may be designed for low resolution and high robustness (i.e., large filters and windows), while the second stage may be tuned for higher resolution and accuracy. A plurality of tracking stages may additionally be used in combination with tracking motion in a plurality of coordinates. In another example, shown in FIG. 8B, the second stage of motion tracking may use patterned data images in differing coordinates. This method can additionally be applied to a third dimensional coordinate as shown in FIG. 8C.

As mentioned above, speckle tracking is a carrier based motion tracking method implemented by tracking the position of a kernel (section) of ultrasound speckles that are a result of ultrasound interference and reflections from scanned objects. The synthetically applied pattern of speckles/artifacts is fairly similar over small motions, which allows for tracking the motion of the speckle kernel within a search window (or region) over time. The search window is preferably a window within which the kernel is expected to be found, assuming normal tissue motion. Preferably, the search window is additionally dependent on the frame rate of the ultrasound data. A smaller search window can be used with a faster frame rate, assuming the same tissue velocity. The size of the kernel affects the resolution of the motion measurements. For example, a smaller kernel will result in higher resolution. Motion from speckle tracking can be calculated with various algorithms such as sum of absolute difference (SAD) or normalized cross correlation.

Figure 2:
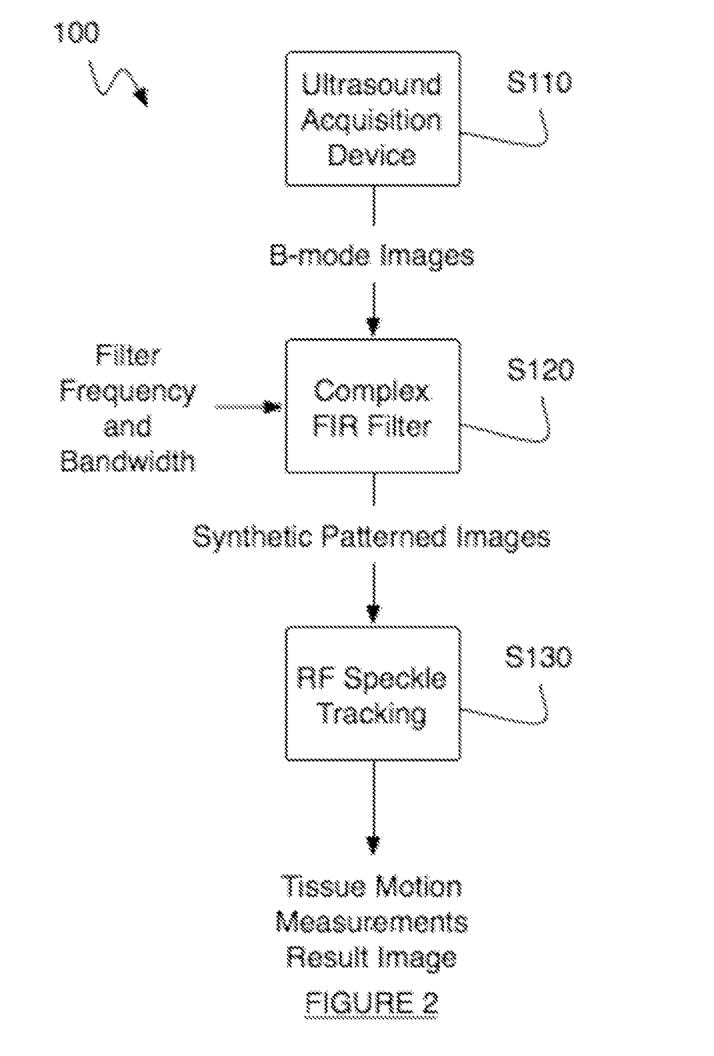
FIG. 2 is an exemplary representation of a first preferred embodiment of the invention.

As shown in FIGS. 1 and 2, one variation of the method preferably applies the pattern jointly to x and y directional coordinates/components of the collected data image. The patterned 2D image is preferably processed during Step S130.

Figure 3:
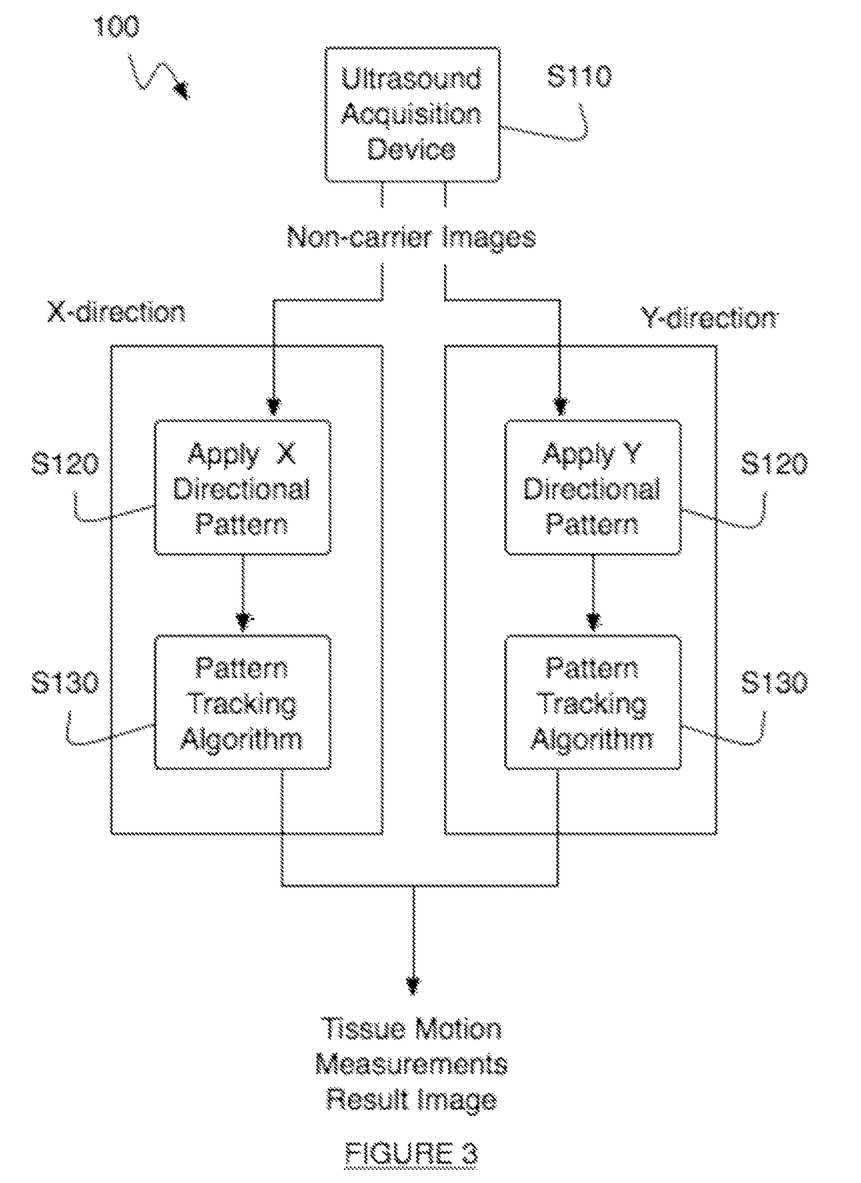
FIGS. 3-5 are a schematic representation of preferred embodiments of the invention based on directional components of an ultrasound image.
Figure 4:
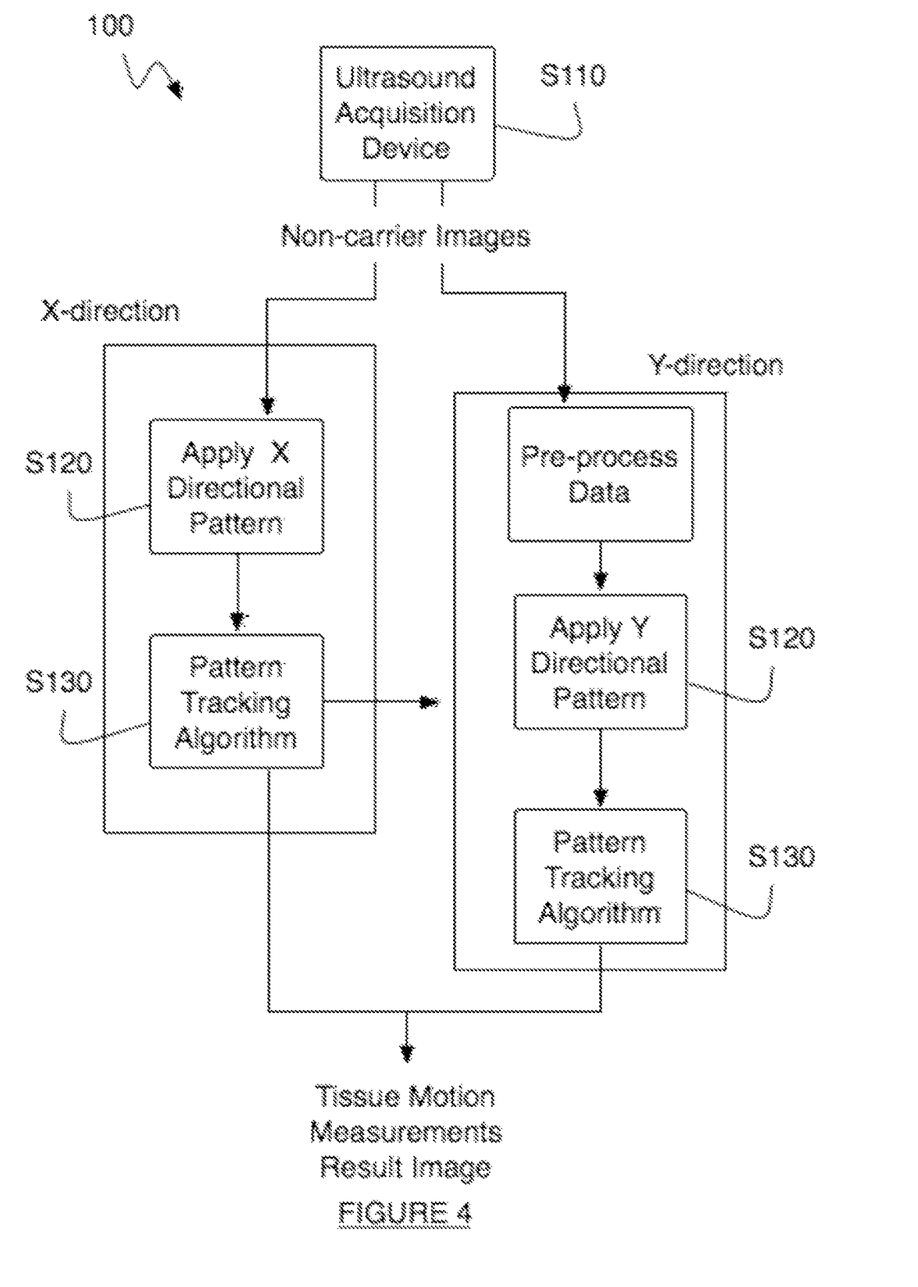

Another variation preferably applies the pattern to at least one direction coordinate (e.g., to a x directional component and y directional component). Preferably, for each directional coordinate the non-carrier data image is patterned, and then the pattern motion is calculated for each corresponding coordinate. The calculated pattern motion for the directional coordinate are preferably combined to form the 2D tissue motion measurements. For example, the x directional coordinate and the y directional coordinate preferably each have a patterned data image and are each processed for motion in a particular coordinate direction, as shown in FIG. 3. In a related variation, the data images for the directional components are preferably patterned and processed in series. More preferably, the results of pattern motion in a first coordinate direction are preferably used to modify patterning parameters and/or processing parameters for processing in a second coordinate direction, as shown in FIG. 4. The images for the second direction may additionally be pre-processed (e.g., resampled) based on motion calculations in the first direction. The tracking parameters such as tracking location seeding, window size, and search size are preferably adjusted according to the first direction motion image. Filter parameters may additionally be modified according to the first direction motion image.

Figure 5:
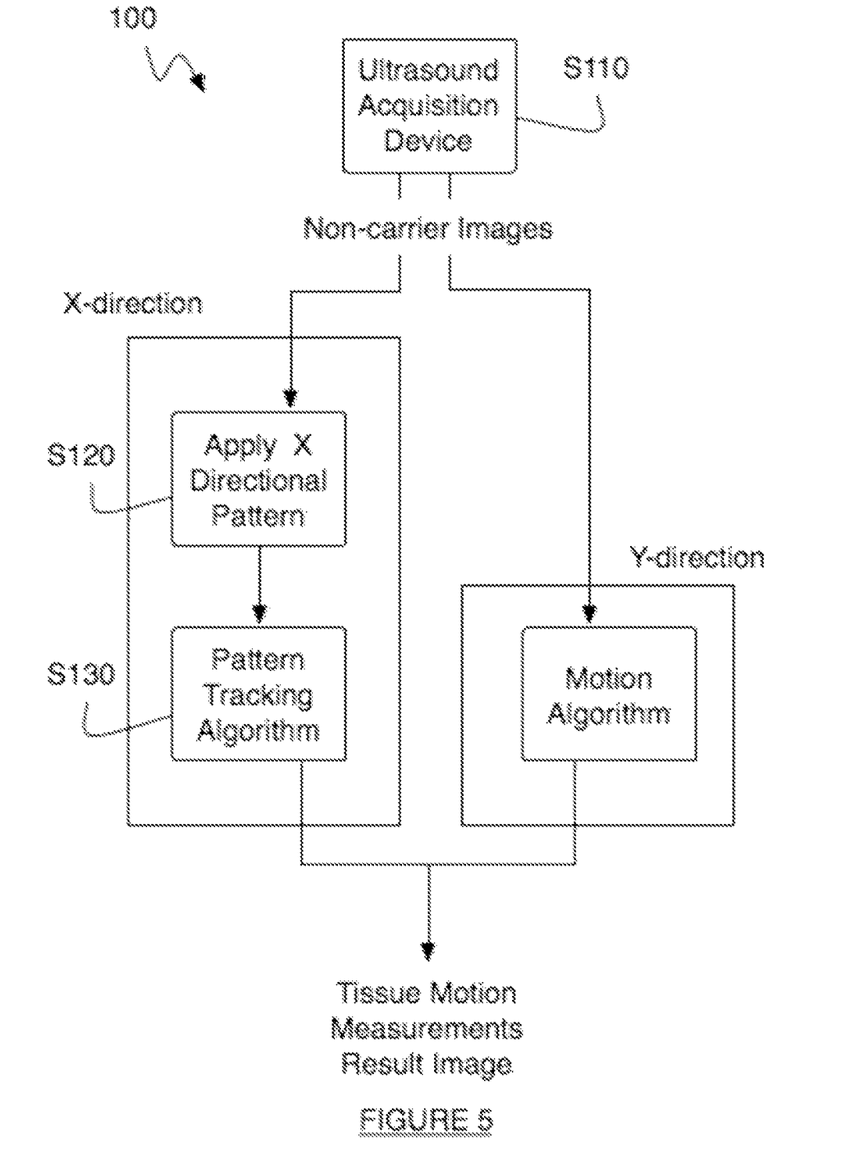

As shown in FIG. 5, another variation preferably patterns one directional component, and leaves the other directional component of an image un-patterned. Motion is then preferably calculated for the first directional component with the patterned image and second directional component with the un-patterned image. The 2D motion can preferably be calculated from the motion image calculations for the two directional components.

Figure 6:
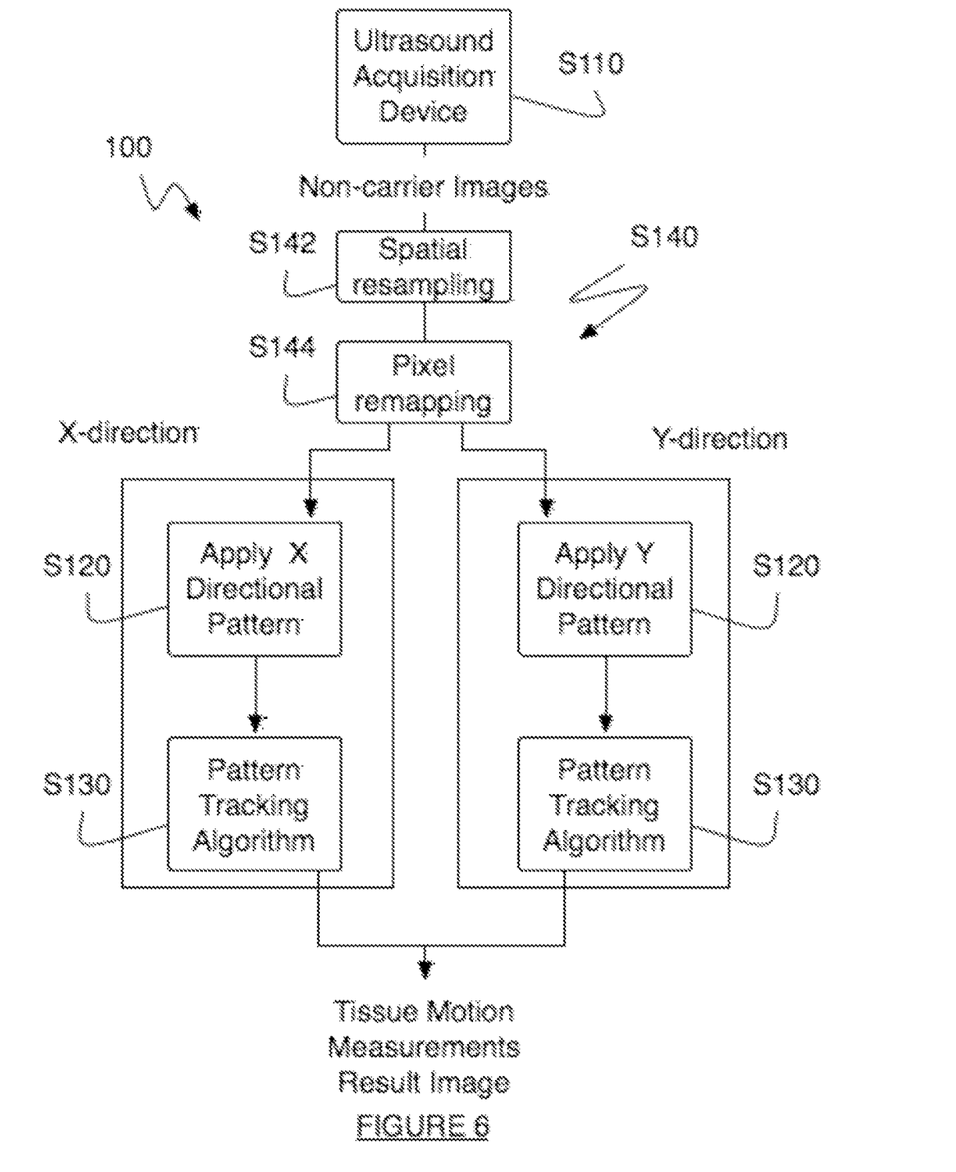
FIG. 6 is a schematic representation of a preferred embodiment with preprocessing of the non-carrier data images.

Additionally, the method 100 preferably includes preprocessing the non-carrier data images S140 as shown in FIG. 6, which functions to condition and transform the data to a suitable data format for patterning. Preprocessing in some cases is used to compensate for processing or formatting previously applied to the non-carrier data images. The preprocessing is preferably performed prior to patterning and processing motion. Preprocessing the non-carrier data S140 preferably includes spatial resampling of non-carrier data S142 and remapping pixels of non-carrier data S144. Spatial resampling preferably functions to convert object coordinates. The spatial order of the pixels of the non-carrier data images is preferably converted to an optimal spatial order of the carrier based motion tracking technique For example some inputs may be in scan converted or object coordinates (e.g., x y coordinates), where speckle size and orientation varies with location thus creating challenges for pattern generation and tracking. Spatial resampling preferably resamples the images along beam coordinates (e.g., range and angle), which functions to make speckle characteristics spatially invariant and more suitable for processing (e.g., speckle tracking). Pixel remapping preferably functions to alter pixel values for improved processing. As the non-carrier data is often in a different image space than that of a typical image processed with the carrier based motion tracking technique, the image space of the non-carrier data image is preferably altered for better results. The pixels are preferably remapped to an optimal pixel value space of the carrier based motion tracking technique. For example, B-mode ultrasound images may be dynamic range compressed and measured echo amplitudes are preferably mapped for display using a log function to show a large dynamic range of echoes. Such a mapping of intensities is not ideal for carrier-based motion tracking techniques. A power function or any other suitable function is preferably applied to the B-mode ultrasound images to effectively reverse the dynamic range compression.

Figure 9A:
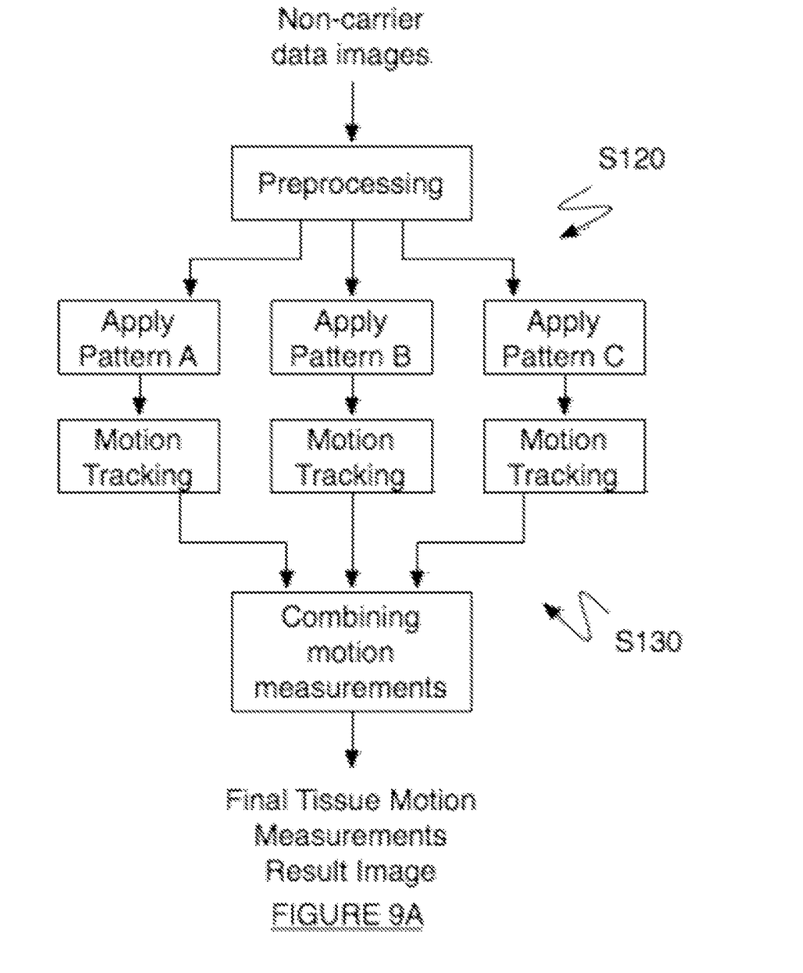
FIGS. 9A and 9B is a schematic representation of multi-pattern processing of non-carrier data images.
Figure 9B:
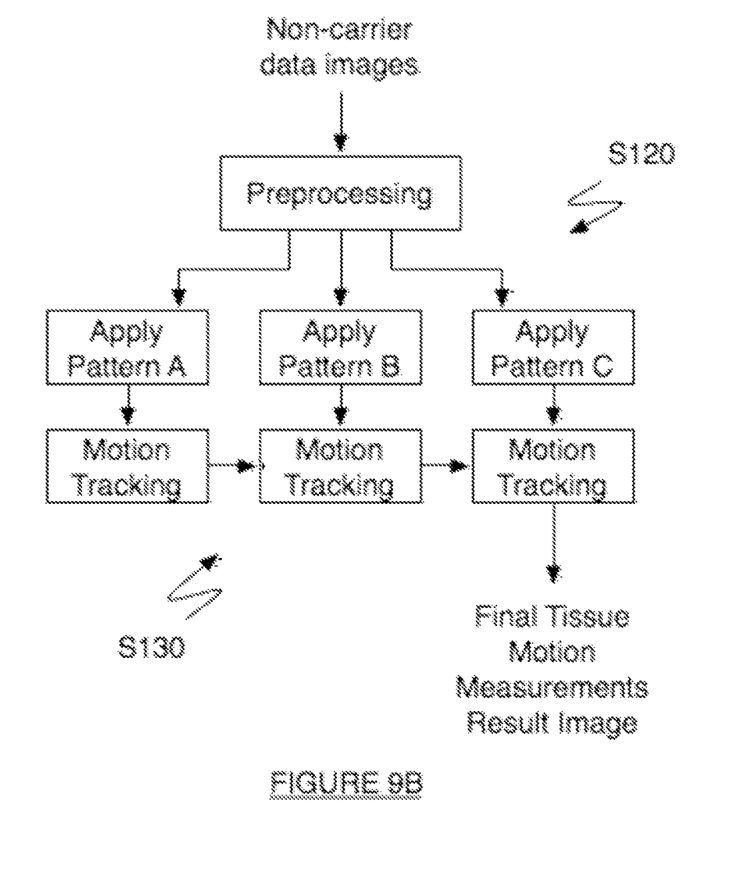

Additionally or alternatively, the method 100 may include patterning the data image with at least two differing patterns as shown in FIGS. 9A and 9B. The multi-pattern processing of non-carrier data images preferably functions to leverage the varying benefits of different types of patterns and filters that can be applied to the non-carrier data images. The differing patterns may include unique pattern parameters for an applied filter such as center frequency, bandwidth of a complex filter, or any suitable pattern parameter. The differing patterns preferably generate different synthetic speckles/patterns on the non-carrier data images which in turn alter the motion processing capabilities. The intermediary motion images from a plurality of patterning stages can preferably combined to generate a final motion image, which functions to utilize the various advantages of different patterns. Motion image calculations from an initial pattern stage may additionally be used to adjust the calculation of motion from at least a second pattern stage as shown in FIG. 9B.

Additionally, the method 100 for measuring ultrasound image motion with synthetic speckle patterns can preferably be used with any suitable variation of ultrasound processing. The method may be used in combination with dynamic ultrasound processing, dynamic ultrasound acquisition, fast-acquisition with coded transmit signals, fast-acquisition with frame subset acquisition, frame selection, multi-stage speckle tracking, partial 3D ultrasound, and/or any suitable variation of ultrasound processing. Dynamic processing preferably includes modifying a processing parameter based on calculated object motion. Dynamic processing may additionally include the calculating of data quality metrics. Dynamic acquisition preferably includes modifying a parameter of data generation based on object motion, and preferably includes a feedback loop to the data acquisition system. Fast-acquisition with coded transmit signals includes multiplexing a first transmit beam signal with at least one transmit beam signal, transmitting the multiplexed transmit beam signals, receiving at least one receive beam corresponding to the transmit beam signals, and demultiplexing the received beams to their respective signals during ultrasound data acquisition. Fast-acquisition with frame subset acquisition preferably includes collecting local subsets of a full frame at a first rate, calculating object motion for the local subset and combining object motion information of the local subsets to form a full frame image at a second rate lower than the first rate. Frame selection preferably includes capturing ultrasound data at a data acquisition rate, setting an inter-frameset data rate, selecting frames to form a plurality of framesets, and processing the data from memory at the controlled data rates. Frame selection may additionally include setting an intra-frameset data rate. Multi-stage speckle tracking preferably includes calculating a first stage of object motion by tracking displacement between a first patterned image and a second patterned image and calculating a second stage of object motion using the calculated object motion of the first stage. The first stage is preferably calculated on images with a coarse image resolution and the second stage is preferably calculated on images with a finer image resolution. Partial 3D ultrasound preferably includes acquiring partial 3D ultrasound images by scanning a target plane and scanning at least one offset plane.

Figure 10:
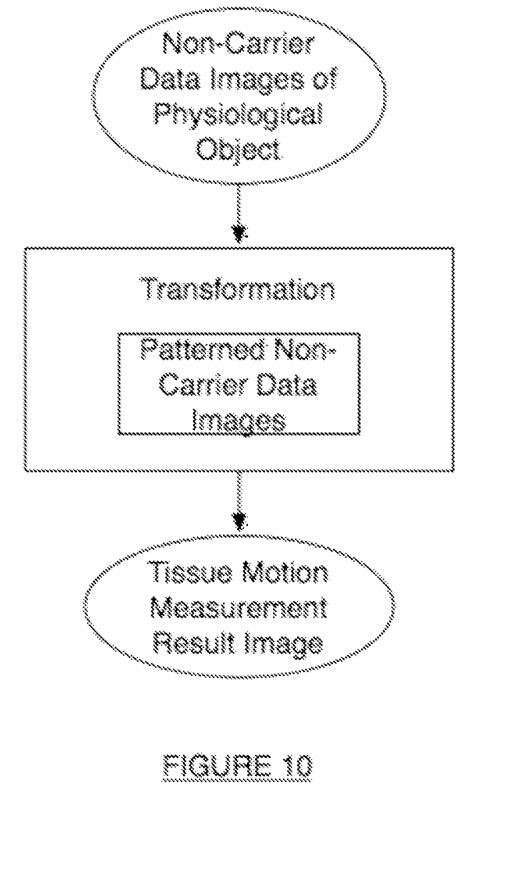
FIG. 10 is a flowchart representation of a transformation of a preferred embodiment of the invention.

As shown in FIG. 10, the method preferably facilitates a transformation of data representing physiological tissue to a data representation of motion or in some preferred variations a motion image. The transformation preferably begins with the collection of data lacking carrier information (i.e., non-carrier data images) such as a B-mode ultrasound data. The data image preferably represents a tissue or organs such as a human heart or other biological tissue. The transformation includes an initial transformation of the data representation by applying a synthetic pattern onto the non-carrier data images. The patterned non-carrier data images are then processed using a carrier based motion tracking technique such as speckle tracking. Speckle tracking, though not directly compatible with the non-carrier data images, is a highly accurate and robust technique for tracking motion which can be applied to the non-carrier data images after the initial transformation. The results of the carrier-based motion tracking are preferably motion images representing the motion of tissue or detected object.

Figure 11:
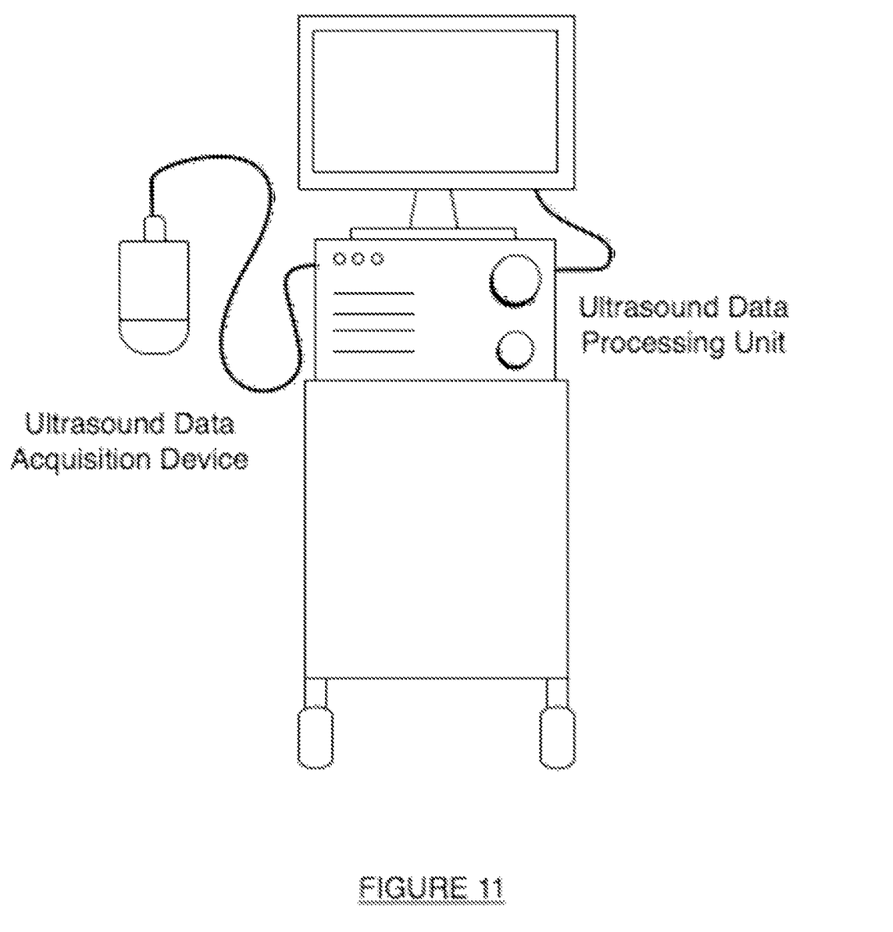
FIG. 11 is a schematic representation of a particular machine that implements a preferred embodiment of the invention.

As shown in FIG. 11, the method is preferably implemented by a particular machine that includes an ultrasound data acquisition device and an ultrasound processing unit. The ultrasound data acquisition device is preferably a medical tool used to acquire B-mode (or non-carrier) ultrasound data. The ultrasound data acquisition device preferably includes at least one ultrasound transducer that transmits and detects at least one ultrasound beam, and preferably includes at least one beamformer that controls ultrasound beam characteristics. The ultrasound processing unit is preferably a unit directly in communication with the ultrasound data acquisition device, by a physical cable connection, a wireless communication connection, or any other suitable connection. The ultrasound processing unit may alternatively be in indirect communication such as in the case where the ultrasound data is stored or buffered. The ultrasound processing unit preferably transforms the non-carrier ultrasound data to a motion image calculated with a carrier-based motion tracking technique. The ultrasound processing unit preferably provides the motion image to a display, printer, or any other suitable output.

The method may be implemented, either in part or in whole, through computer-readable instructions stored on a computer-readable medium, such as RAMs, ROMs, flash memory, EEPROMs, optical devices (CD or DVD), hard drives, floppy drives, or any suitable device. The instructions may be executed by computer-executable components for acquiring and processing ultrasound images with synthetic speckle patterns. The computer-executable component is preferably a processor but the instructions may alternatively or additionally be executed by any suitable dedicated hardware device.

As a person skilled in the art will recognize from the previous detailed description and from the figures and claims, modifications and changes can be made to the preferred embodiments of the invention without departing from the scope of this invention defined in the following claims.

I claim:

1. A method for measuring ultrasound image motion for biomedical applications comprising:
    an ultrasound processor is programmed to perform:
    acquiring ultrasound images without carrier properties;
    applying at least one complex filter to the ultrasound images to generate a synthetic speckle pattern, the at least one complex filter comprising at least one unique pattern parameter identifying an aspect of the ultrasound images to which the at least one complex filter will be applied wherein the at least one unique pattern parameter is at least one of a center frequency parameter and a bandwidth parameter;
    deriving artificial carrier properties for the images from the synthetic speckle pattern;
    producing speckle tracking data with a speckle tracking algorithm operating on the images and the artificial carrier properties;
    wherein the producing speckle tracking data includes:
    producing a first set of speckle tracking data according to a first set of speckle tracking parameters to generate a first stage result; and
    producing at least a second set of speckle tracking data according to a second set of speckle tracking parameters to generate a second stage result;
    wherein producing at least a second set of speckle tracking data comprises using the first stage result
    extracting motion tracking parameters from the speckle tracking data; and
    creating images representing motions based on the motion parameters.

2. The method of claim 1, wherein the ultrasound images comprise B-mode ultrasound images.

3. The method of claim 1, wherein producing the speckle tracking data includes processing the first set in a first coordinate and processing the second set in at least a second coordinate.

4. The method of claim 1, further comprising spatially resampling pixels of at least one ultrasound image to an optimal spatial order for the speckle tracking algorithm.

5. The method of claim 4, further comprising remapping pixels of at least one ultrasound image to an optimal pixel value space of the speckle tracking algorithm.

6. The method of claim 1, wherein generating the synthetic speckle pattern includes generating a first pattern in a first image coordinate; and wherein producing the speckle tracking data includes operating on at least one ultrasound image in the first image coordinate to generate a result in the first image coordinate.

7. The method of claim 6, wherein generating the synthetic speckle pattern includes generating a second pattern in at least a second image coordinate, and wherein producing the speckle tracking data includes operating on at least one ultrasound image in at least the second image coordinate to generate a result in at least the second image coordinate.

8. The method of claim 7, wherein generating the second pattern in at least a second image coordinate utilizes the result in the first image coordinate.

* * * * *